(12) United States Patent
Sueda

(10) Patent No.: US 7,121,291 B2
(45) Date of Patent: Oct. 17, 2006

(54) CHECK VALVE, AUXILIARY CIRCULATING DEVICE AND METHOD FOR DRIVING THE AUXILIARY CIRCULATING DEVICE

(75) Inventor: Taijiro Sueda, Hiroshima (JP)

(73) Assignee: Hiroshima University, Kagamiyama (JP)

( * ) Notice: Subject to any disclaimer, the term of this patent is extended or adjusted under 35 U.S.C. 154(b) by 408 days.

(21) Appl. No.: 10/683,287

(22) Filed: Oct. 14, 2003

(65) Prior Publication Data

US 2004/0163714 A1    Aug. 26, 2004

(30) Foreign Application Priority Data

Oct. 17, 2002    (JP)    ............... 2002-302855

(51) Int. Cl.
*F16K 15/00*    (2006.01)
*A61M 1/10*    (2006.01)

(52) U.S. Cl. ................ 137/1; 137/528; 137/533; 137/565.15

(58) Field of Classification Search ............. 137/528, 137/533, 565.15
See application file for complete search history.

(56) References Cited

U.S. PATENT DOCUMENTS

| | | | | | |
|---|---|---|---|---|---|
| 2,809,660 | A | * | 10/1957 | Becker | 137/514.3 |
| 3,048,165 | A | * | 8/1962 | Norton | 623/3.22 |
| 3,518,702 | A | * | 7/1970 | La Russa | 623/3.22 |
| 4,813,452 | A | * | 3/1989 | Smith | 137/542 |
| 4,902,291 | A | * | 2/1990 | Kolff | 623/3.21 |
| 5,271,898 | A | * | 12/1993 | Wolf et al. | 422/64 |
| 5,693,091 | A | * | 12/1997 | Larson et al. | 623/3.27 |
| 2004/0069353 | A1 | * | 4/2004 | Pickelman | 137/540 |

* cited by examiner

*Primary Examiner*—Ramesh Krishnamurthy
(74) *Attorney, Agent, or Firm*—Oliff & Berridge, PLC

(57) ABSTRACT

A check valve includes a casing member, a tear-drop shaped ball member installed in the casing member, a latching member which is formed at an inner wall of the casing member and an airtight valve which is formed at an inner wall of the casing member. When forward flux occurs, the ball member is fixed at the latching members absolutely to circulate the forward flux stably. When backward flux occurs, the ball member is latched at the airtight member to close the casing member and thus, to suppress the backward flux.

12 Claims, 2 Drawing Sheets

CHECK VALVE, AUXILIARY CIRCULATING DEVICE AND METHOD FOR DRIVING THE AUXILIARY CIRCULATING DEVICE

BACKGROUND OF THE INVENTION

1. Field of the Invention

This invention relates to a check valve, an auxiliary circulating device such as a blood auxiliary circulating device which is typified by an auxiliary artificial heart utilizing the check valve, and to a method for driving the auxiliary circulating device.

2. Description of the Prior Art

Such various properties as durability, retention for blood circulation, blood compatibility (antithrombogenicity, antihemolysis), and histocompatibility are required for a check valve to be employed for an blood auxiliary circulating device such as an auxiliary artificial heart to support a dysfunctional heart. As of now, as the check valve are exemplified a mechanical valve such as a ball valve, a tilting disk valve and a two lobe valve.

At present, the two lobe valve is mainly employed as the check valve because the valve can make large central flow and large efficient valve opening area easily, and requires only small space in closing motion. With the two lobe valve, however, blood may be coagulated and accreted at the hinge of the disk of the valve.

In view of high durability and high degree of freedom of material selectivity, in contrast, it is desired to employ the ball valve as the check valve. With the ball valve, however, when spherical ball members are latched at latching members in the casing member of the valve, the ball members may be slipped away from the latching members by forward flow flux due to the insufficient latching. Therefore, blood can not be flowed stably, resulting in thromboembolism.

FIG. 1 is a schematic view showing a conventional ball valve. As shown in FIG. 1, when forward flux occurs, in the casing member 1, the spherical ball member 2 is moved upstream and latched at the latching members 3. In this case, the forward flux is flowed through the space around the ball member 2. However, the ball member 2 is slipped away from the latching member 3 due to the backward vortex flow for the upstream from the forward flux because the ball member 2 is made spherical. As a result, the forward flux may be blocked with the slipped ball member 2, resulting in the thromboembolism.

SUMMERY OF THE INVENTION

It is an object of the present invention to provide a check valve which can prevent backflow of circulating substance such as blood and generate the stable forward flux of the circulating substance, and provide an auxiliary circulating device utilizing the check valve and a method for driving the auxiliary circulating device.

In order to achieve the above object, this invention relates to a check valve comprising;

a casing member, a ball member installed in the casing member, a latching member which is formed at an inner wall of the casing member and generates forward flux while the ball member is latched, and an airtight valve which is formed at an inner wall of the casing member and closes the casing member to suppress backward flux while the ball member is latched, wherein the ball member is made in tear-drop shape.

According to the present invention, since the ball member of the check valve is made in tear-drop shape, instead of the conventional spherical shape, the ball member can be latched at the latching member absolutely when forward flux occurs, so that the disturbance of the slipping away of the ball member can be prevented. When backward flux occurs, the ball member is latched at the airtight container and closes the casing member, the backward flux can be suppressed. As a result, the circulating substance such as blood can be flowed stably.

Moreover, an auxiliary circulating device according to the present invention is characterized by comprising a check valve as mentioned above. That is, the auxiliary circulating device of the present invention is characterized by comprising an auxiliary circulating device main body and a check valve joined with the main body, the check valve comprising;

a casing member, a ball member installed in the casing member, a latching member which is formed at an inner wall of the casing member and generates forward flux while the ball member is latched, and an airtight valve which is formed at an inner wall of the casing member and closes the casing member to suppress backward flux while the ball member is latched, wherein the ball member is made in tear-drop shape.

A driving method of auxiliary circulating device according to the present invention is characterized by comprising a check valve as mentioned above. That is, the driving method is characterized by comprising the steps of:

joining a check valve including a casing member and a ball member installed in the casing member with an auxiliary circulating device main body, latching the ball member at a latching member formed at an inner wall of the casing member to generate forward flux, and latching the ball member at an airtight member formed at an inner wall of the casing member, to close the casing member and thus, suppress backward flux.

Other features and advantages of the present invention will be described in detail, hereinafter.

BRIEF DESCRIPTION OF THE DRAWINGS

For better understanding of the present invention, reference is made to the attached drawings, wherein.

DESCRIPTION OF THE PREFERRED EMBODIMENTS

Figure 1:
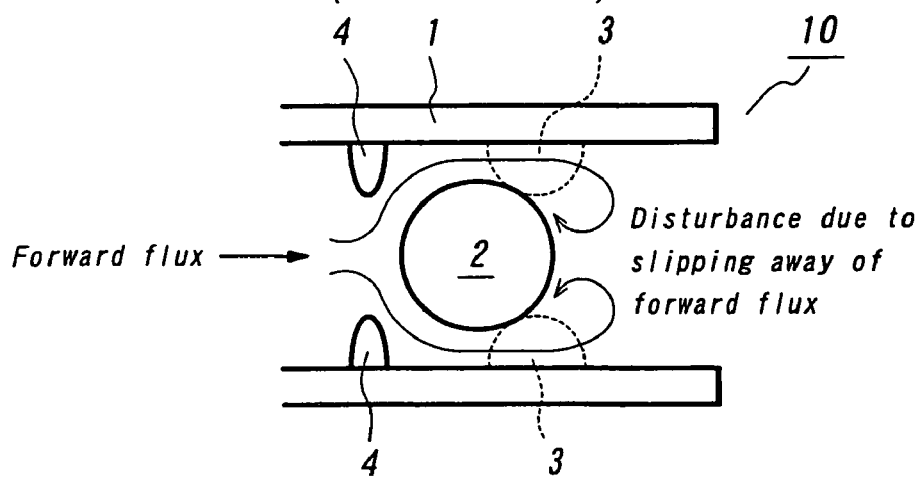
FIG. 1 is a schematic view showing a conventional ball valve.
Figure 2:
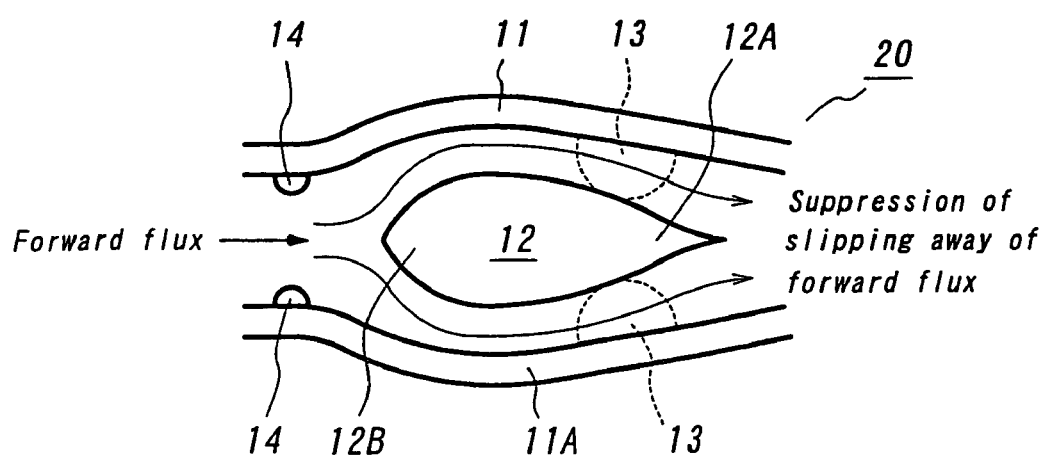
FIG. 2 is a schematic view showing a check valve according to the present invention.
Figure 3:
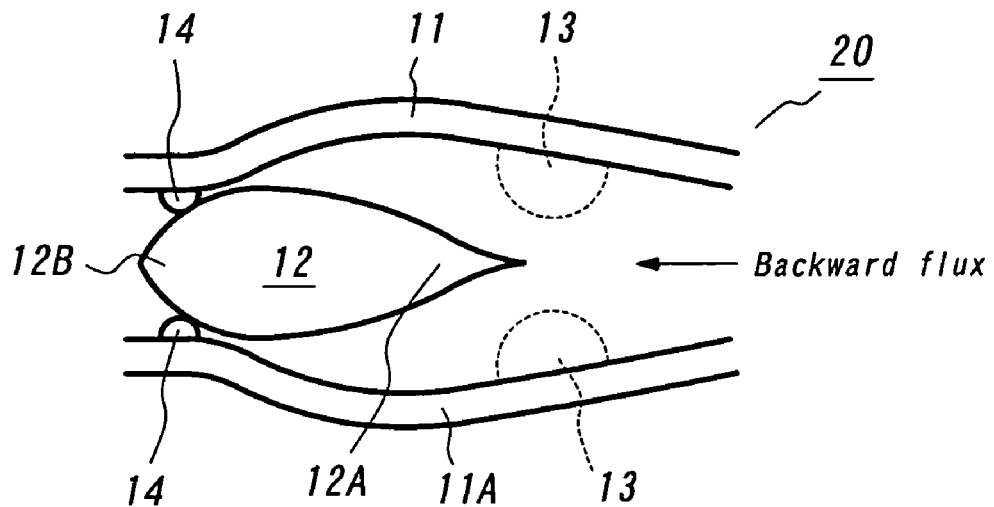
FIG. 3 is a schematic view showing the check valve in different configuration.

This invention will be described in detail with reference to the accompanying drawings. FIGS. 2 and 3 are schematic views showing a check valve according to the present invention. FIG. 2 shows a state where forward flux occurs, and FIG. 3 shows a state where backward flux occurs. As is apparent from FIGS. 2 and 3, the check valve 20 includes a casing member 11, a tear-drop shaped ball member 12 installed in the casing member 11, a latching member 13 formed at the inner wall of the casing member 11 and an airtight member 14 formed at the inner wall of the casing member 11.

With the ball member 12, the inclined level of the forward portion 12A is set smaller than the inclined level of the backward portion 12B, so that the ball member 12 is made in tear-drop shape for the forward side. The ball member 12 may be made for the backward side. In this embodiment, since the ball member 12 is made for the forward side as shown in FIGS. 2 and 3, the ball member 12 can be latched at the latching member 13 absolutely.

With the casing member 11, the side portion 11A to install the ball member 12 is made in parallel with the contour of the ball member 12. Therefore, when the ball member 12 is latched at the latching member 13, stable flux can be generated around the ball member 12, so the circulating substance such as blood can be flowed stably in the forward side.

Next, the driving principle of the check valve 20 illustrated in FIGS. 2 and 3 will be described. As shown in FIG. 2, when the forward flux occurs, the ball member 12 is moved upstream along the forward flux to the latching member 13. In this embodiment, since the ball member 12 is made in tear-drop shape, different from the conventional sphere ball member, as shown in FIGS. 2 and 3, the forefront of the ball member 12 is pinched at the latching member 13, so that the ball member 12 is latched at the latching member 13. In this case, since the ball member 12 is latched at the latching member 13 absolutely, the disturbance of the forward flux due to the slipping away from the latching member 13 can be prevented.

Since the portion 11A of the casing member 11 to install the ball member 12 is made in parallel with the contour the ball member 12, the forward flux is flowed through the almost uniform space between the casing member 11 and the ball member 12. Therefore, the intended circulating substance such as blood can be flowed stably in the forward side.

As shown in FIG. 3, when backward flux occurs, the ball member 12 is moved downstream along the backward flux and latched at the airtight member 14 to close the casing member 11. Therefore, the backward flux can be suppressed with the check valve 20.

Figure 4:
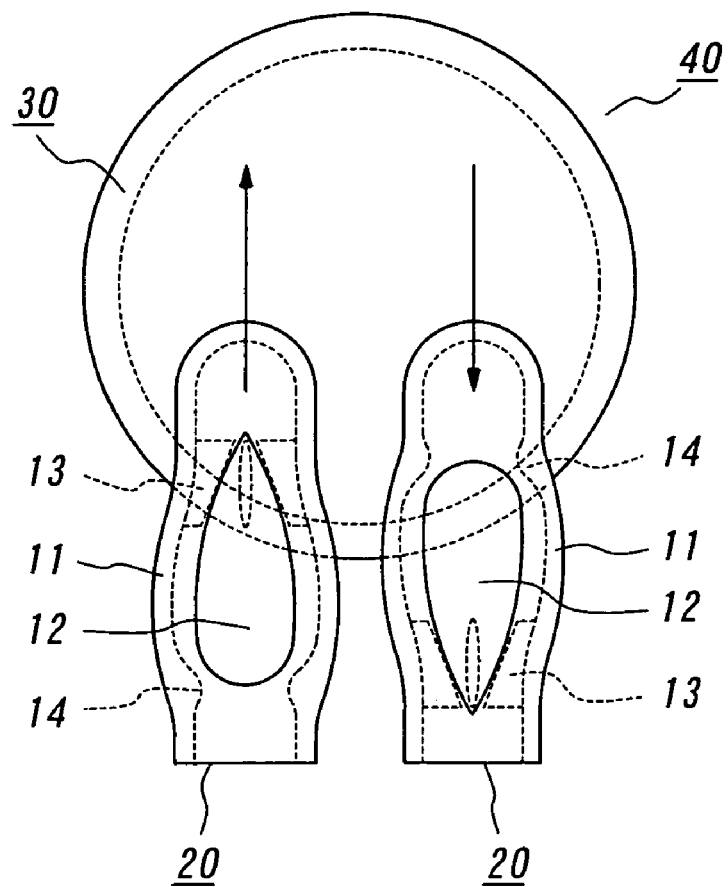
FIG. 4 is a top plan view showing an auxiliary circulating device according to the present invention.

FIG. 4 is a top plan view showing an auxiliary circulating device according to the present invention. An auxiliary circulating device 40 illustrated in FIG. 4 includes an auxiliary circulating device main body 30 and check valves 20 joined with the main body 30. The check valves 20 is constituted from the one as illustrated in FIGS. 2 and 3. In FIG. 4, the arrow designates the flowing direction (forward direction) of a circulating substance. As mentioned above, since the check valves 20 include their respective tear-drop shaped ball members 12, the forward flux can be stabilized and the backward flux can be suppressed due to the configuration of the ball members 12, so that the intended circulating substance can be flowed stably through the main body 30.

The auxiliary circulating device main body 30 may be constructed of various blood circulating device main bodies, so that various blood circulating devices with the functions of the check valve can be provided. Particularly, if the auxiliary circulating device main body 30 is made of an auxiliary artificial heart main body, an auxiliary artificial heart which can circulate blood stably can be provided.

Although the present invention was described in detail with reference to the above examples, this invention is not limited to the above disclosure and every kind of variation and modification may be made without departing from the scope of the present invention.

As mentioned above, according to the present invention can be provided a check valve which can prevent backflow of circulating substance such as blood and generate the stable forward flux of the circulating substance, and provided an auxiliary circulating device utilizing the check valve and a method for driving the auxiliary circulating device.

What is claimed is:

1. A check valve comprising;
   a casing member,
   a movable valve body installed in said casing member,
   a latching member which is formed at an inner wall of said casing member and generates forward flux while the movable valve body is latched, and
   an airtight valve seat which is formed at an inner wall of said casing member and closes said casing member to suppress backward flux while the movable valve body is seated,
   wherein the movable valve body is made in tear-drop shape, an inclined level of a forward portion of the movable valve body that is configured to engage the latching member being set smaller than an inclined level of a backward portion of the movable valve body that configured to engage the airtight valve seat, the tear-drop shape facilitating absolute latching of the movable valve body at the latching member and stable flow of a circulating substance past the forward portion.

2. The check valve as defined in claim 1, wherein a portion of said casing member to install the movable valve body is made in almost parallel with the contour of the movable valve body.

3. An auxiliary circulating device comprising an auxiliary circulating device main body and a check valve joined with said main body,
   said check valve comprising;
   a casing member,
   a movable valve body installed in said casing member,
   a latching member which is formed at an inner wall of said casing member and generates forward flux while the movable valve body is latched, and
   an airtight valve seat which is formed at an inner wall of said casing member and closes said casing member to suppress backward flux while the movable valve body is seated,
   wherein the movable valve body is made in tear-drop shape, an inclined level of a forward portion of the movable valve body that is configured to engage the latching member being set smaller than an inclined level of a backward portion of the movable valve body that is configured to engage the airtight valve seat, the tear-drop shape facilitating absolute latching of the movable valve body at the latching member and stable flow of a circulating substance past the forward portion.

4. The auxiliary circulating device as defined in claim 3, wherein a portion of said casing member to install the movable valve body is made in almost parallel with the contour of the movable valve body.

5. The auxiliary circulating device as defined in claim 3, wherein said auxiliary circulating device main body is constructed of a blood auxiliary circulating device main body, to complete a blood auxiliary circulating device.

6. The auxiliary circulating device as defined in claim 5, wherein said blood auxiliary circulating device main body is constructed of an auxiliary artificial heart main body, to complete an artificial heart.

7. The auxiliary circulating device as defined claim 4, wherein said auxiliary circulating device main body is constructed of a blood auxiliary circulating device main body, to complete a blood auxiliary circulating device.

8. A method for driving an auxiliary circulating device, comprising the steps of:
joining a check valve including a casing member and a movable valve body installed in said casing member with an auxiliary circulating device main body,
latching the movable valve body at a latching member formed at an inner wall of said casing member to generate forward flux, and
seating the movable valve body at an airtight valve seat formed at an inner wall of said casing member, to close said casing member and thus, suppress backward flux,
wherein the movable valve body is made in a tear-drop shape, an inclined level of a forward portion of the movable valve body that is configured to engage the latching member being set smaller than an inclined level of a backward portion of the movable valve body that is configured to engage the airtight valve seat, the tear-drop shape facilitating absolute latching of the movable valve body at the latching member and stable flow of a circulating substance past the forward portion.

9. The driving method as defined in claim 8, wherein a portion of said casing member to install the movable valve body is made in almost parallel with the contour of the movable valve body.

10. The driving method as defined in claim 8, wherein said auxiliary circulating device main body is constructed of a blood auxiliary circulating device main body, to complete a blood auxiliary circulating device.

11. The driving method as defined in claim 10, wherein said blood auxiliary circulating device main body is constructed of an auxiliary artificial heart main body, to complete an artificial heart.

12. The driving method as defined in claim 9, wherein said auxiliary circulating device main body is constructed of a blood auxiliary circulating device main body, to complete a blood auxiliary circulating device.

* * * * *